US012648742B2

(12) United States Patent
Inoue

(10) Patent No.: US 12,648,742 B2
(45) Date of Patent: Jun. 9, 2026

(54) NUCLEAR MEDICINE DIAGNOSTIC APPARATUS

(71) Applicant: CANON MEDICAL SYSTEMS CORPORATION, Tochigi (JP)

(72) Inventor: Motohiro Inoue, Otawara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 502 days.

(21) Appl. No.: 17/810,479

(22) Filed: Jul. 1, 2022

(65) Prior Publication Data

US 2023/0071056 A1 Mar. 9, 2023

(30) Foreign Application Priority Data

Sep. 8, 2021 (JP) ................................. 2021-145964

(51) Int. Cl.
$A61B\ 6/03$ (2006.01)
$A61B\ 6/42$ (2024.01)
$G01T\ 1/20$ (2006.01)
$G06T\ 11/00$ (2006.01)

(52) U.S. Cl.
CPC ............ *A61B 6/037* (2013.01); *A61B 6/4258* (2013.01); *G01T 1/2018* (2013.01); *G06T 11/005* (2013.01); *G06T 2207/10104* (2013.01)

(58) Field of Classification Search
CPC ...................... A61B 6/037; G06T 2207/10104
See application file for complete search history.

(56) References Cited

U.S. PATENT DOCUMENTS

| | | | | |
|---|---|---|---|---|
| 5,272,344 | A * | 12/1993 | Williams | ............... A61B 6/037 |
| | | | | 250/252.1 |
| 8,598,536 | B2 | 12/2013 | Jarron et al. | |
| 8,921,796 | B1 | 12/2014 | Arseneau et al. | |
| 9,354,332 | B2 | 5/2016 | Zwaans et al. | |
| 10,027,340 | B1 * | 7/2018 | Weisenberger | ......... H03M 1/12 |
| 10,244,992 | B2 | 4/2019 | Wu | |
| 2007/0090297 | A1 * | 4/2007 | Rutten | .................. G01T 1/2985 |
| | | | | 250/363.03 |
| 2015/0302614 | A1 * | 10/2015 | Xie | ........................ G06T 11/006 |
| | | | | 702/181 |
| 2021/0199823 | A1 * | 7/2021 | Li | ........................ A61B 6/5258 |

\* cited by examiner

*Primary Examiner* — Uzma Alam
*Assistant Examiner* — Shun Lee
(74) *Attorney, Agent, or Firm* — Oblon, McClelland, Maier & Neustadt, L.L.P.

(57) ABSTRACT

A nuclear medicine diagnostic apparatus according to a present embodiment includes a plurality of units of detector that detects gamma rays, and each of the units of detector includes detection circuitry, generation circuitry, and first production circuitry. The detection circuitry detects an analog signal based on a result of detecting the gamma rays. The generation circuitry generates a clock signal. The first production circuitry produces time information by converting the analog signal into a digital signal on the basis of the clock signal.

10 Claims, 4 Drawing Sheets

FIG.5

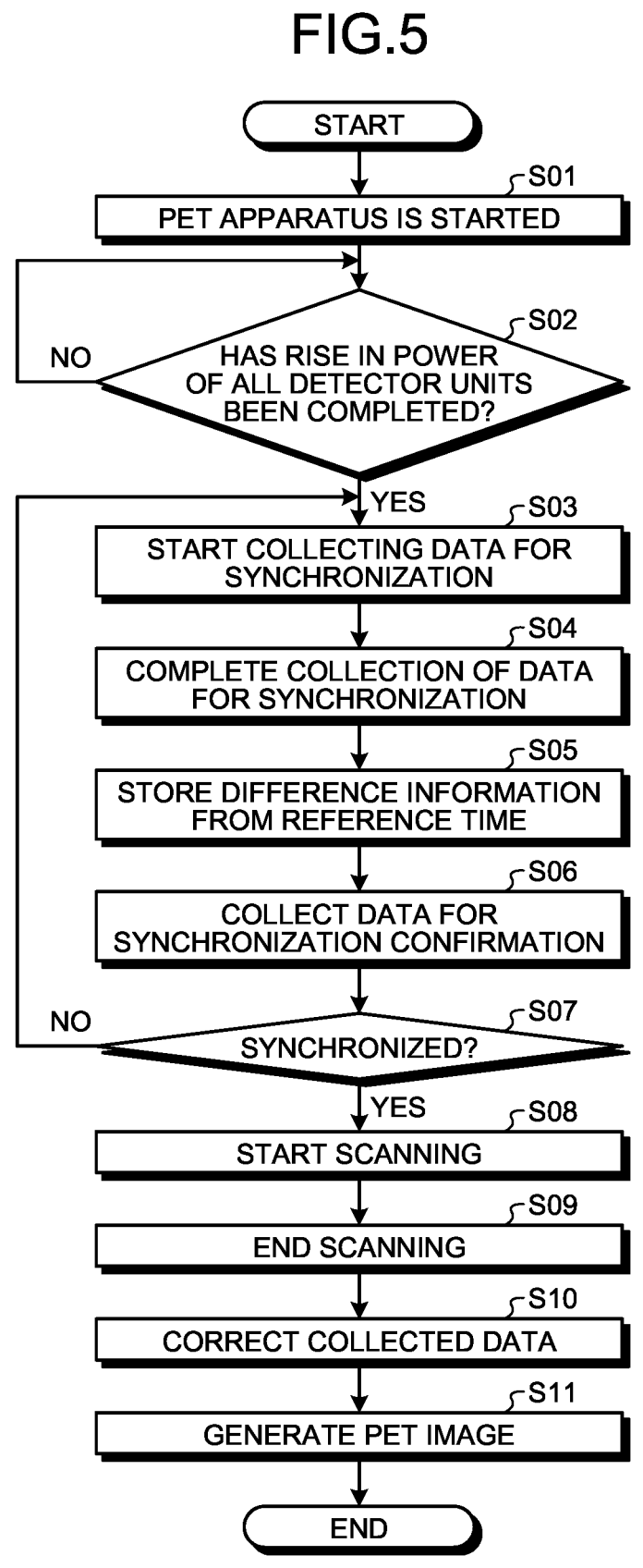

START

PET APPARATUS IS STARTED — S01

HAS RISE IN POWER OF ALL DETECTOR UNITS BEEN COMPLETED? — S02

NO

YES

START COLLECTING DATA FOR SYNCHRONIZATION — S03

COMPLETE COLLECTION OF DATA FOR SYNCHRONIZATION — S04

STORE DIFFERENCE INFORMATION FROM REFERENCE TIME — S05

COLLECT DATA FOR SYNCHRONIZATION CONFIRMATION — S06

SYNCHRONIZED? — S07

NO

YES

START SCANNING — S08

END SCANNING — S09

CORRECT COLLECTED DATA — S10

GENERATE PET IMAGE — S11

END

NUCLEAR MEDICINE DIAGNOSTIC APPARATUS

CROSS-REFERENCE TO RELATED APPLICATIONS

This application is based upon and claims the benefit of priority from Japanese Patent Application No. 2021-145964, filed on Sep. 8, 2021; the entire contents of which are incorporated herein by reference.

FIELD

Embodiments disclosed herein generally relate to a nuclear medicine diagnostic apparatus.

BACKGROUND

Conventionally, a positron emission tomography (PET) apparatus specifies sets of counting information that counts annihilation gamma rays at substantially the same time from counting information of annihilation gamma rays detected by a plurality of units of detector, and generates a PET image on the basis of coincidence counting information in which the specified sets of counting information are correlated.

In such a PET apparatus, it is important to synchronize time information between the units of detector in order to obtain a high-quality PET image. Therefore, for example, a technique of supplying each of the units of detector with a clock signal output from a single oscillator is known.

However, in such a technique, it is necessary to prepare a cable with equal-length wiring for supplying a clock signal or a synchronization signal between the oscillator and each unit of detector, which increases device price and reduces reliability. Such problems are not limited to the PET apparatus, but may occur in other nuclear medicine diagnostic apparatuses as well.

BRIEF DESCRIPTION OF THE DRAWINGS

FIG. 5 is a flowchart illustrating a procedure for processing synchronization between units of detector, which is performed by the PET apparatus according to the present embodiment.

DETAILED DESCRIPTION

A nuclear medicine diagnostic apparatus according to a present embodiment includes a plurality of units of detector that detects gamma rays, and each of the units of detector includes detection circuitry, generation circuitry, and first production circuitry. The detection circuitry detects an analog signal based on a result of detecting the gamma rays. The generation circuitry generates a clock signal. The first production circuitry produces time information by converting the analog signal into a digital signal on the basis of the clock signal.

Hereinafter, embodiments of a nuclear medicine diagnostic apparatus disclosed in the present application are described in detail with reference to the drawings. Hereinafter, an embodiment of a PET apparatus is described as an example of the nuclear medicine diagnostic apparatus.

Embodiment

Figure 1:
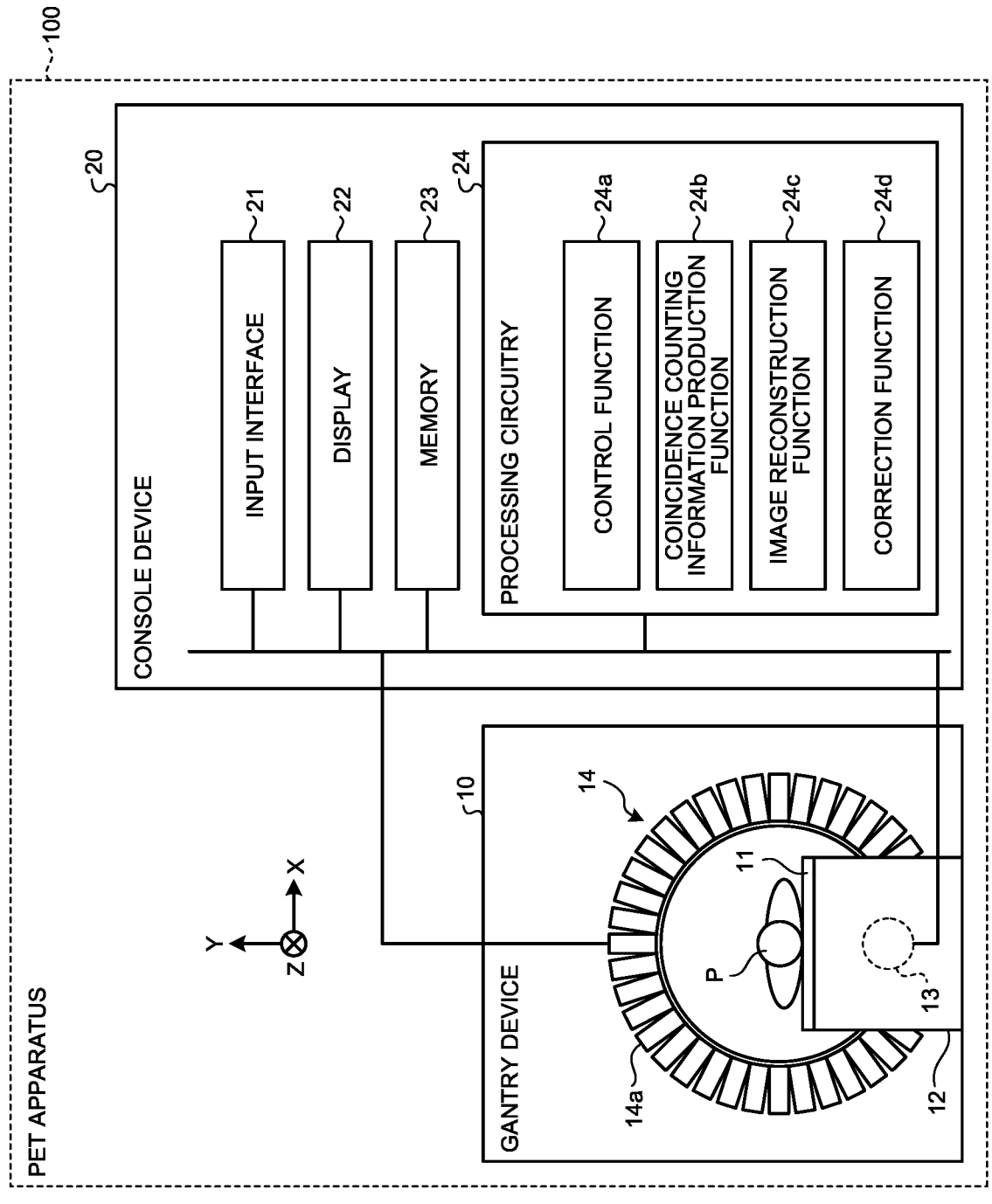
FIG. 1 is a diagram illustrating a configuration example of a PET apparatus according to the present embodiment.

FIG. 1 is a diagram illustrating a configuration example of a PET apparatus according to the present embodiment;

For example, as illustrated in FIG. 1, a PET apparatus 100 according to the present embodiment includes a gantry device 10 and a console device 20.

The gantry device 10 detects annihilation gamma rays emitted when positrons emitted from a tracer administered to a subject P are annihilated with electrons, and collects counting information by counting the detected annihilation gamma rays. The gantry device 10 has a cylindrical opening formed to penetrate the gantry device 10 in the horizontal direction, and detects annihilation gamma rays emitted from the subject P disposed in the opening. Hereinafter, a direction along an axis of the cylindrical opening of the gantry device 10 is defined as a Z-axis direction, a horizontal direction orthogonal to the Z-axis direction is defined as an X-axis direction, and a vertical direction orthogonal to the Z-axis direction is defined as a Y-axis direction.

Specifically, the gantry device 10 includes a couchtop 11, a couch 12, a couch driving mechanism 13, and a PET detector 14.

The couchtop 11 is a bed on which the subject P is placed. For example, the couchtop 11 is formed in a rectangular flat plate shape and disposed so that a longitudinal direction is parallel to the Z-axis direction.

The couch 12 supports the couchtop 11 so as to be movable in the X-axis direction, the Y-axis direction, and the Z-axis direction.

The couch driving mechanism 13 is provided inside or outside the couch 12 and moves the couchtop 11 supported by the couch 12. For example, when the subject P is imaged, the couch driving mechanism 13 moves the couchtop 11, on which the subject P is placed, to the opening of the gantry device 10. For example, in a state in which the position of the couch 12 is fixed, the couch driving mechanism 13 moves the couchtop 11 on the couch 12. Alternatively, for example, the couch driving mechanism 13 may include a moving base and move the couchtop 11 together with the couch 12 on the moving base.

The PET detector 14 detects annihilation gamma rays emitted from the subject P. Then, the PET detector 14 produces counting information including the detection position, energy value, and detection time of the detected annihilation gamma rays, and transmits the produced counting information to the console device 20.

Specifically, the PET detector 14 includes a plurality of detector units 14a arranged in a ring shape around a Z-axis to surround the opening formed in the gantry device 10, and each detector unit 14a detects annihilation gamma rays and produces counting information.

For example, the detector unit 14a is a photon counting type or Anger type detector and includes scintillators, photodetectors, and light guides.

The scintillator converts the incident annihilation gamma rays emitted from the positrons in the subject P into scintillation light and outputs the scintillation light. For example, the scintillator is formed of scintillator crystals suitable for energy measurement, such as LaBr3, LYSO, LSO, LGSO, BGO, GAGG, and LuAG. For example, the scintillators are arranged two-dimensionally.

The photodetector detects the scintillation light output from the scintillator and converts the scintillation light into an analog signal. For example, the photodetector is configured by a photomultiplier tube such as a photomultiplier (PMT) or a silicon photomultiplier (SiPM).

The light guide is formed of a plastic material or the like with excellent light transmission properties and transmits the scintillation light output from the scintillator to the photodetector.

The detector unit 14a may be a non-Anger type detector in which scintillators and photodetectors are optically coupled in a one-to-one manner and there are no light guides. Alternatively, for example, the detector unit 14a may not be an indirect conversion detector using scintillators, but a direct conversion detector using semiconductors such as CZT, CdTe, Ge, and Si.

Then, the detector unit 14a produces counting information including the detection position, energy value, and detection time of the annihilation gamma rays on the basis of the analog signal output from the photodetector.

For example, the detector unit 14a specifies a plurality of photodetectors having converted scintillation light into an analog signal at the same timing. Then, the detector unit 14a specifies the position of a scintillator, where the annihilation gamma rays have been incident, as the detection position of the annihilation gamma rays. For example, the detector unit 14a specifies the position of the scintillator where the annihilation gamma rays have been incident by performing a center-of-gravity calculation on the basis of the position of the photodetector and the intensity of the analog signal. Alternatively, for example, when the sizes of the scintillator and the photodetector correspond to each other, the detector unit 14a may specify the position of a scintillator, which corresponds to a photodetector from which output is obtained, as the position of the scintillator where the annihilation gamma rays have been incident.

Furthermore, for example, the detector unit 14a specifies the energy value of the annihilation gamma rays by integrally calculating the intensity of the analog signal output from the photodetector. Alternatively, for example, the detector unit 14a may specify the energy value of the annihilation gamma rays by measuring the time (time over threshold (ToT)) over which the intensity of the analog signal output from the photodetector exceeds a preset threshold and performing a nonlinear correction using the measured time.

Furthermore, for example, the detector unit 14a specifies the time when the scintillation light is detected by the photodetector as the detection time of the annihilation gamma rays. The detection time may be an absolute time or an elapsed time from the start of imaging.

The console device 20 receives various operations on the PET apparatus 100 from an operator and controls the operation of the PET apparatus 100 on the basis of the received operations. Specifically, the console device 20 includes an input interface 21, a display 22, a memory 23, and processing circuitry 24. The respective parts of the console device 20 are connected via a bus. Although an example in which the gantry device 10 and the console device 20 are provided separately from each other is described, the console device 20 or a part of the components of the console device 20 may be included in the gantry device 10.

The input interface 21 receives various input operations from the operator, converts the received input operations into electric signals, and outputs the electric signals to the processing circuitry 24. For example, the input interface 21 is implemented by a mouse, a keyboard, a trackball, a switch, a button, or a joystick for setting imaging conditions, a region of interest (ROI), and the like, a touch pad for performing an input operation by touching an operation surface, a touch screen with integrated display screen and touch pad, non-contact input circuitry using an optical sensor, a voice input interface, or the like. For example, the input interface 21 may be provided on the gantry device 10. Furthermore, for example, the input interface 21 may include a tablet terminal or the like capable of wirelessly communicating with the console device 20 itself. Furthermore, the input interface 21 is not limited to only those with physical operating components such as a mouse and a keyboard. For example, an example of an input interface 21 also includes an electrical signal processing circuitry that receives electrical signals corresponding to input operations from an external input device provided separately from the console device 20 and outputs the electrical signals to processing circuitry 24.

The display 22 displays various types of information. For example, the display 22 displays a PET image produced by the processing circuitry 24, a graphical user interface (GUI) for receiving various operations from the operator, and the like. For example, the display 22 is a liquid crystal display or a cathode ray tube (CRT) display. For example, the display 22 may be provided on the gantry device 10. Furthermore, for example, the display 22 may be a desktop type, or may include a tablet terminal or the like capable of wirelessly communicating with the console device 20 itself.

The memory 23 stores various data used in the PET apparatus 100. For example, the memory 23 is implemented by a semiconductor memory element such as a random access memory (RAM) and a flash memory, a hard disk, an optical disc, or the like.

The processing circuitry 24 controls the operation of the entire PET apparatus 100. Specifically, the processing circuitry 24 includes a control function 24a, a coincidence counting information production function 24b, an image reconstruction function 24c, and a correction function 24d.

The control function 24a performs overall control of the PET apparatus 100 by controlling each part of the gantry device 10 and the console device 20. For example, the control function 24a moves the couchtop 11 by controlling the couch driving mechanism 13. Furthermore, for example, the control function 24a collects counting information of annihilation gamma rays emitted from the subject P by controlling the PET detector 14, and stores the collected counting information in the memory 23.

The coincidence counting information production function 24b produces coincidence counting information by using counting information produced by the PET detector 14. Specifically, the coincidence counting information production function 24b refers to the counting information stored in the memory 23 and specifies sets of counting information in which annihilation gamma rays have been counted at roughly the same time, on the basis of the detection time of each counting information. Then, the coincidence counting information production function 24b produces coincidence counting information corresponding to the specified sets of counting information, and stores the produced coincidence counting information in the memory 23.

The image reconstruction function 24c reconstructs a PET image on the basis of the coincidence counting information produced by the coincidence counting information production function 24*b*. Specifically, the image reconstruction function 24*c* reconstructs the PET image by reading the coincidence counting information stored in the memory 23 and performing back-projection processing using the read coincidence counting information as projection data. Furthermore, the image reconstruction function 24*c* stores the reconstructed PET image in the memory 23.

The correction function 24*d* is described in detail below.

The processing circuitry 24 is implemented by a processor, for example. In such a case, processing functions of the processing circuitry 24 are stored in the memory 23 in the form of computer programs executable by a computer. The processing circuitry 24 reads the computer programs from the memory 23 and executes the read computer programs, thereby implementing processing functions corresponding to the executed computer programs. In other words, the processing circuitry 24 in the state of reading the computer programs has the processing functions illustrated in the processing circuitry 24 in FIG. 1.

So far, the configuration example of the PET apparatus 100 according to the present embodiment has been described. Under such a configuration, as described above, the PET apparatus 100 specifies sets of counting information in which annihilation gamma rays have been counted at roughly the same time between counting information of the annihilation gamma rays detected by the detector units 14*a*, and generates a PET image on the basis of coincidence counting information in which the specified sets of counting information are correlated.

In such a PET apparatus, it is important to synchronize time information between the detector units 14*a* in order to obtain a high-quality PET image. Therefore, for example, a technique of supplying each of the units of detector with a clock signal output from a single oscillator is known.

However, in such a technique, it is necessary to prepare a cable with equal-length wiring for supplying a clock signal or a synchronization signal between the oscillator and each unit of detector, which increases device price and reduces reliability.

Therefore, the PET apparatus 100 according to the present embodiment is configured to be able to suppress an increase in device price and a decrease in reliability due to synchronization between units of detector.

Specifically, in the present embodiment, each of the detector units 14*a* included in the PET detector 14 includes detection circuitry, generation circuitry, and first production circuitry. The detection circuitry detects an analog signal based on a result of detecting gamma rays. The generation circuitry generates a clock signal. The first production circuitry produces time information by converting the analog signal detected by the detection circuitry into a digital signal on the basis of the clock signal generated by the generation circuitry. The detector unit 14*a* is an example of the unit of detector.

According to such a configuration, by individually providing each detector unit 14*a* with the generation circuitry that generates a clock signal, it is possible to eliminate the need for cables with equal-length wiring required when synchronization is performed using a single oscillator. With this, in the present embodiment, it is possible to suppress an increase in device price and a decrease in reliability due to synchronization between units of detector.

Hereinafter, a configuration example of the PET apparatus 100 according to the present embodiment is described in more detail.

Figure 2:
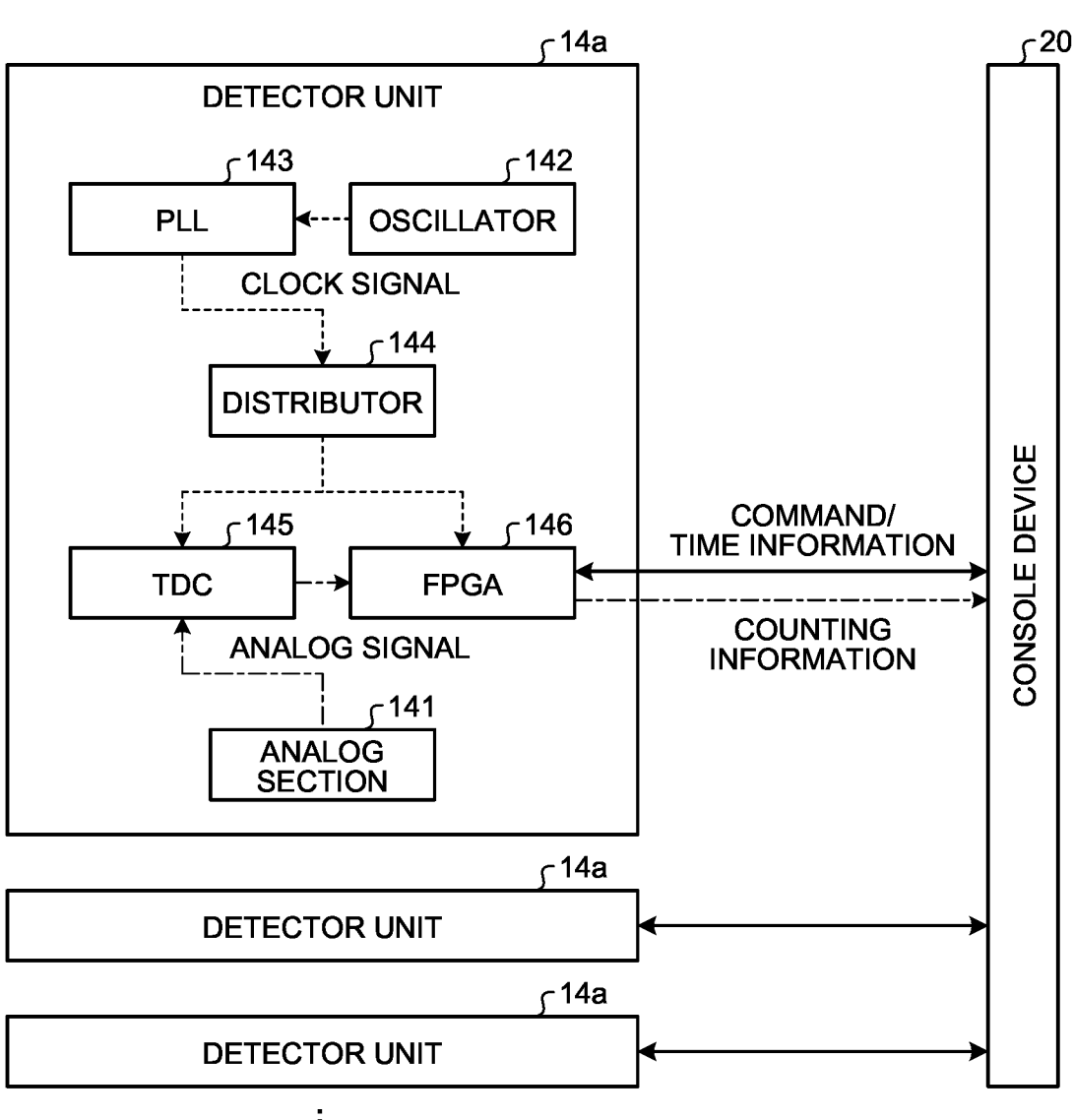
FIG. 2 is a diagram illustrating a configuration example of a detector unit according to the present embodiment.

FIG. 2 is a diagram illustrating a configuration example of the detector unit 14*a* according to the present embodiment.

For example, as illustrated in FIG. 2, each detector unit 14*a* included in the PET detector 14 includes an analog section 141, an oscillator 142, a phase locked loop (PLL) 143, a distributor 144, a time to digital converter (TDC) 145, and a field programmable gate array (FPGA) 146.

The analog section 141 detects an analog signal based on a result of detecting gamma rays. The analog section 141 is an example of detection circuitry.

Specifically, the analog section 141 includes the aforementioned scintillator and photodetector, converts incident annihilation gamma rays emitted from the positrons in the subject P into scintillation light, converts the scintillation light into an analog signal, and outputs the analog signal.

The oscillator 142 generates a clock signal. For example, the oscillator 142 is implemented by circuitry using a natural transducer element such as a quartz transducer element. The oscillator 142 is an example of generation circuitry.

The PLL 143 converts the clock signal generated by the oscillator 142 into a clock signal with a predetermined frequency and outputs the clock signal.

The distributor 144 distributes the clock signal output from the PLL 143 to the TDC 145 and the FPGA 146.

The TDC 145 produces time information by converting the analog signal detected by the analog section 141 into a digital signal on the basis of the clock signal generated by the oscillator 142. The TDC 145 is an example of first production circuitry.

Specifically, the TDC 145 receives the clock signal distributed by the distributor 144 and the analog signal output from the analog section 141, measures the time over which the intensity of the analog signal exceeds a predetermined threshold, and converts the analog signal into a digital signal, thereby producing the time information.

The FPGA 146 produces counting information including the detection position, energy value, and detection time of the aforementioned annihilation gamma rays on the basis of the analog signal output from the analog section 141 and the time information produced by the TDC 145. Then, the FPGA 146 transmits the produced counting information to the console device 20. The FPGA 146 is an example of second production circuitry.

Furthermore, the FPGA 146 acquires the time information produced by the TDC 145, on the basis of a synchronization signal generated by synchronization signal generation circuitry. Then, the FPGA 146 transmits the acquired time information to the console device 20. The FPGA 146 is an example of first acquisition circuitry and second acquisition circuitry.

For example, the synchronization signal generation circuitry is a scintillator included in the analog section 141, and the synchronization signal is a gamma ray produced by the spontaneous decay of the scintillator. In this case, for example, the FPGA 146 acquires time information when gamma rays due to the spontaneous decay of the scintillator are generated. Alternatively, for example, the synchronization signal generation circuitry may be a gamma ray source disposed in the opening of the gantry device 10, and the synchronization signal may be gamma rays emitted from the gamma rays source. Alternatively, for example, the synchronization signal generation circuitry may be the control function 24*a* of the console device 20, and the synchronization signal may be a command transmitted from the control function 24*a*.

Although an example using the FPGA 146 has been described, for example, other processing circuitry implemented by processors such as a central processing unit (CPU), a graphics processing unit (GPU), an application specific integrated circuit (ASIC), a simple programmable logic device (SPLD), and a complex programmable logic device (CPLD) may be used instead of the FPGA 146.

In the present embodiment, the processing circuitry 24 includes the correction function 24*d*.

The correction function 24*d* corrects an offset of time information between a detector unit 14*a* as a reference and another detector unit 14*a* on the basis of time information acquired by the FPGA 146 of the detector unit 14*a* as a reference and the FPGA 146 of the another detector unit 14*a*. The correction function 24*d* is an example of a correction section.

The following is a specific example of synchronization between units of detector, which is performed by the PET apparatus 100 according to the present embodiment. For convenience of explanation, it is assumed that three detector units 14*a* are included in the PET detector 14 as the detector units 14*a*.

Figure 3:
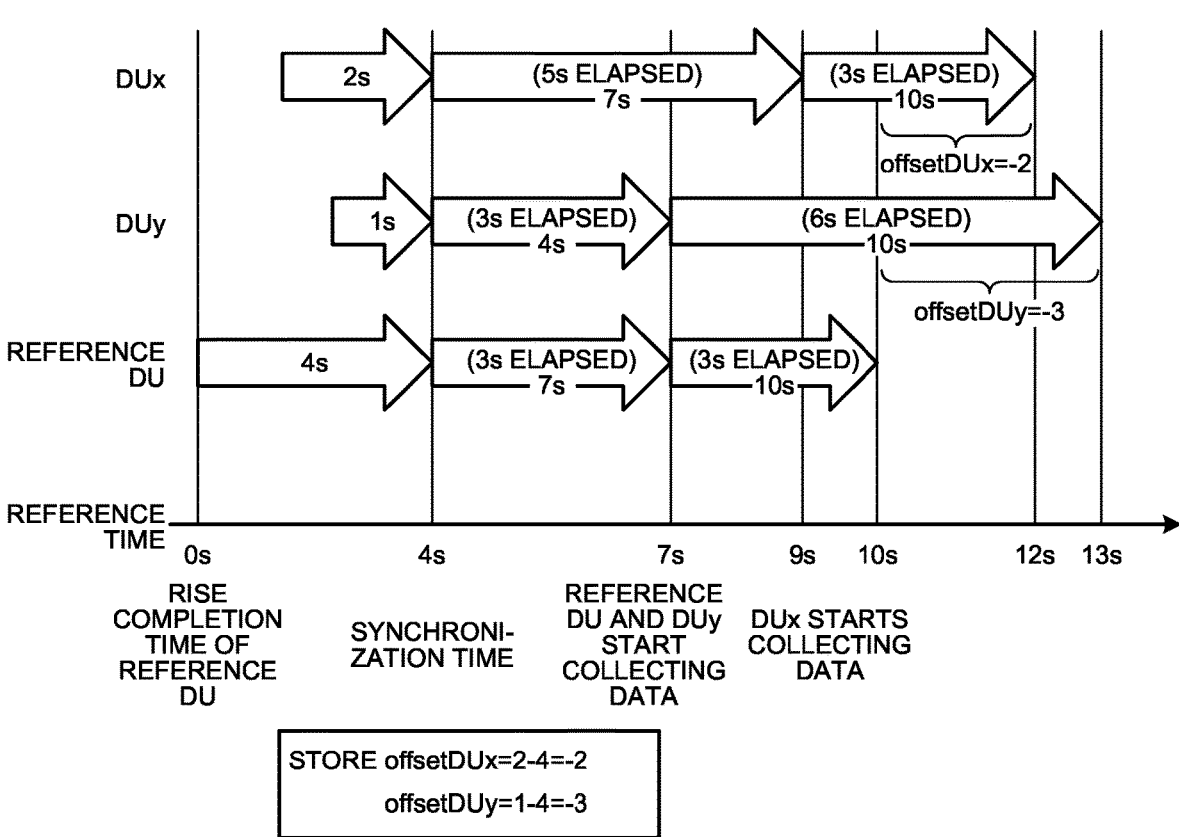
FIG. 3 is a diagram illustrating an example of synchronization between units of detector, which is performed by the PET apparatus according to the present embodiment.

FIG. 3 is a diagram illustrating an example of synchronization between units of detector, which is performed by the PET apparatus 100 according to the present embodiment.

For example, when the detector units 14*a* are used as in the present embodiment, there may be variations in the time from power-on of the PET apparatus 100 to completion of the power rise due to factors such as individual differences between the detector units 14*a*.

Therefore, in the present embodiment, the FPGA 146 in each detector unit 14*a* acquires time information produced by the TDC 145, on the basis of a synchronization signal generated by the synchronization signal generation circuitry after the rise in power of all of the detector units 14*a*.

For example, as illustrated in FIG. 3, when a detector unit 14*a*, whose rise is completed earliest, is set as a reference DU, it is assumed that DUx completes its rise 2 seconds after the rise completion time of the reference DU and DUy completes its rise 3 seconds after the rise completion time of the reference DU. In this case, the FPGA 146 for each of the reference DU, the DUx, and the DUy acquires the time information produced by the TDC 145 after the rise in power of all of the reference DU, the DUx, and the DUy, for example, when gamma rays due to the spontaneous decay of a scintillator are generated.

Then, for example, as illustrated in FIG. 3, it is assumed that gamma rays are generated due to the spontaneous decay of the scintillator when 4 seconds have elapsed from the rise completion time of the reference DU. In that case, time information produced by the reference DU is "4 seconds", but time information produced by the DUx is "2 seconds" with a delay of 2 seconds from the time information of the reference DU, and time information produced by the DUy is "1 second" with a delay of 3 seconds from the time information of the reference DU.

In the present embodiment, the correction function 24*d* stores difference information between the time information acquired by the FPGA 146 of the detector unit 14*a* as a reference and time information acquired by the FPGA 146 of the other detector unit 14*a* in the memory 23 as a synchronization process. The memory 23 is an example of a storage section.

For example, as illustrated in FIG. 3, the correction function 24*d* stores, in the memory 23, difference information (offsetDUx=2−4=−2) between the time information produced by the reference DU and the time information produced by DUx. Furthermore, the correction function 24*d* stores, in the memory 23, difference information (offsetDUy=1−4=−3) between the time information produced by the reference DU and the time information produced by the DUy.

Thereafter, there may be variations in the time between the transmission of a command to start a scan from the console device 20 and the start of data collection due to factors such as individual differences between the detector units 14*a*.

For example, as illustrated in FIG. 3, the reference DU and the DUy each start collecting data when 3 seconds have elapsed from the time of synchronization, and the DUx starts collecting data when 5 seconds have elapsed from the time of synchronization. In that case, time information produced by the reference DU is "7 seconds" by adding 3 seconds to 4 seconds at the time of synchronization, time information produced by DUx is "7 seconds" by adding 5 seconds to 2 seconds at the time of synchronization, and the time information produced by DUy is "4 seconds" by adding 3 seconds to 1 second at the time of synchronization.

Thereafter, in the present embodiment, the correction function 24*d* corrects an offset of time information between the detector units 14*a* by using the difference information stored in the memory 23.

Specifically, the correction function 24*d* uses the difference information and corrects a detection time included in the counting information generated by the FPGA 146 of the other detector unit 14*a* so as to match the detection time with a detection time included in the counting information produced by the FPGA 146 of the detector unit 14*a* as a reference.

For example, as illustrated in FIG. 3, the correction function 24*d* corrects a detection time included in the counting information generated by the FPGA 146 of the DUx so as to match the detection time with a detection time included in the counting information produced by the FPGA 146 of the reference DU. Furthermore, the correction function 24*d* corrects a detection time included in the counting information produced by the FPGA 146 of the DUy so as to match the detection time with a detection time included in the counting information produced by the FPGA 146 of the reference DU.

For example, as illustrated in FIG. 3, when the detection time of the counting information produced by the FPGA 146 of the DUx is 12 seconds, the correction function 24*d* corrects the detection time to "10 seconds" obtained by subtracting 2 seconds from 12 seconds. Furthermore, when the detection time of the counting information produced by the FPGA 146 of the DUy is 13 seconds, the correction function 24*d* corrects the detection time to "10 seconds" obtained by subtracting 3 seconds from 13 seconds.

In the present embodiment, the correction function 24*d* uses a linear equation representing the relationship between the time information and an elapsed time defined for each frequency of the clock signal, and corrects an offset of time information caused by a frequency offset of a clock signal between the detector units 14*a*.

Figure 4:
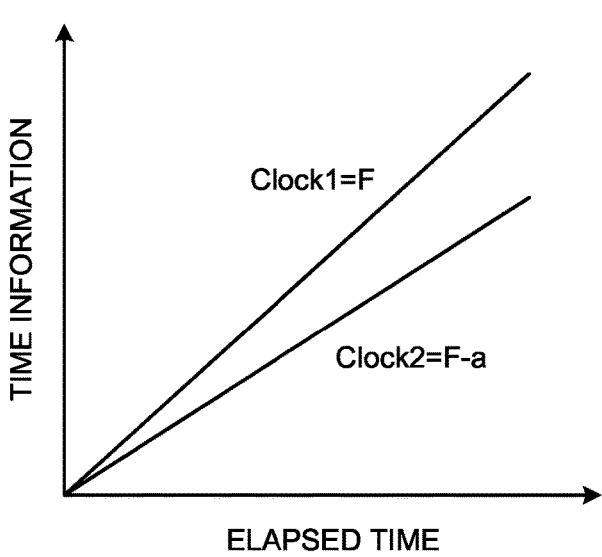
FIG. 4 is a diagram illustrating an example of correction of time information, which is performed by a correction function according to the present embodiment.

FIG. 4 is a diagram illustrating an example of correction of time information, which is performed by the correction function 24*d* according to the present embodiment.

For example, as illustrated in FIG. 4, when there is a frequency offset of the clock signal between the detector units 14*a*, an offset occurs in time information according to an elapsed time. Therefore, for example, the correction function 24*d* uses a linear equation representing the relationship between the time information and the elapsed time predefined for each frequency of the clock signal, and corrects the time information of the other detector unit 14*a* to match a time-dependent change of time information in the number of clocks of the reference DU.

When the correction using the linear equation is difficult due to factors such as jitter or temperature change, the synchronization process may be performed on the basis of gamma rays or the like each time during the standby time or before scanning.

Next, a procedure for processing synchronization between units of detector, which is performed by the PET apparatus 100 according to the present embodiment will be described.

FIG. 5 is a flowchart illustrating a procedure for processing synchronization between the units of detector, which is performed by the PET apparatus 100 according to the present embodiment.

For example, as illustrated in FIG. 5, in the present embodiment, when the PET apparatus 100 is started (step S01) and the rise in the power of all the detector units 14*a* has been completed (Yes at step S02), each detector unit 14*a* starts collecting data for synchronization (step S03). Specifically, the FPGA 146 in each detector unit 14*a* acquires the time information produced by the TDC 145, on the basis of the synchronization signal generated by the synchronization signal generation circuitry.

After the collection of the data for synchronization is completed (step S04), the processing circuitry 24 of the console device 20 stores difference information between the time information produced by each detector unit 14*a* and a reference time in the memory 23 (step S05). Specifically, the correction function 24*d* of the processing circuitry 24 stores, in the memory 23, difference information between the time information acquired by the FPGA 146 of the detector unit 14*a* as a reference and the time information acquired by the FPGA 146 of the other detector unit 14*a*. Since counting information collected together with time information as the data for synchronization may be used, for example, as data for pre-operation inspection of the PET apparatus 100 because it includes the detection position, energy value, and detection time of gamma rays.

Thereafter, each detector unit 14*a* collects data for synchronization confirmation (step S06). Specifically, the FPGA 146 in each detector unit 14*a* re-acquires the time information produced by the TDC 145 on the basis of the synchronization signal generated by the synchronization signal generation circuitry.

Then, the processing circuitry 24 of the console device 20 verifies whether the detector units 14*a* have been synchronized (step S07). Specifically, on the basis of the time information re-acquired by the FPGA 146 of each detector unit 14*a*, the correction function 24*d* of the processing circuitry 24 verifies that the correction of the offset of the time information using the difference information stored in the memory 23 is performed correctly.

When the verification result confirms that the detector units 14*a* have not been synchronized (No at step S07), the processes of steps S03 to S06 are repeated until it is confirmed that the detector units 14*a* are synchronized.

When it is confirmed that the detector units 14*a* have been synchronized (Yes at step S07), the processing circuitry 24 of the console device 20 starts a scan (step S08). Specifically, the control function 24*a* of the processing circuitry 24 collects counting information on annihilation gamma rays emitted from the subject P by controlling the PET detector 14.

After the scanning is ended (step S09), the processing circuitry 24 of the console device 20 corrects the collected data (step S10). Specifically, the correction function 24*d* of the processing circuitry 24 uses the difference information and corrects a detection time included in the counting information generated by the FPGA 146 of the other detector unit 14*a* so as to match the detection time with a detection time included in the counting information produced by the FPGA 146 of the detector unit 14*a* as a reference.

Thereafter, the processing circuitry 24 of the console device 20 produces coincidence counting information by using the corrected counting information and generates a PET image on the basis of the produced coincidence counting information (step S11). Specifically, the coincidence counting information production function 24*b* of the processing circuitry 24 produces the coincidence counting information by using the counting information corrected by the correction function 24*d*. Furthermore, the image reconstruction function 24*c* of the processing circuitry 24 reconstructs the PET image on the basis of the coincidence counting information produced by the coincidence counting information production function 24*b*.

As described above, since there is a variation in the time until data collection is started between the detector units 14*a*, the image reconstruction function 24*c* reconstructs the PET image by using data collected after a detector unit 14*a* for the last scan to be started starts the scan.

For example, when the processing circuitry 24 is implemented by a processor, the processes performed by the control function 24*a*, the coincidence counting information production function 24*b*, the image reconstruction function 24*c*, and the correction function 24*d* described above are implemented by, for example, the processing circuitry 24 reading the computer programs corresponding to the processing functions from the memory 23 and executing the read computer programs.

As described above, in the present embodiment, each of the detector units 14*a* included in the PET detector 14 includes the analog section 141, the oscillator 142, and the TDC 145. The analog section 141 detects an analog signal based on a result of detecting gamma rays. The oscillator 142 generates a clock signal. The TDC 145 produces time information by converting the analog signal detected by the analog section 141 into a digital signal on the basis of the clock signal generated by the oscillator 142.

According to such a configuration, by individually providing the oscillator 142 for each detector unit 14*a*, it is possible to eliminate the need for cables, connectors, or the like with equal-length wiring required when synchronization is performed using a single oscillator. With this, in the present embodiment, it is possible to suppress an increase in device price, an increase in assembly man-hours, and a decrease in reliability due to synchronization between units of detector.

Furthermore, in the present embodiment, the FPGA 146 in each detector unit 14*a* acquires time information produced by the TDC 145, on the basis of a synchronization signal generated by the synchronization signal generation circuitry. Then, on the basis of time information acquired by the FPGA 146 of the detector unit 14*a* as a reference and time information acquired by the FPGA 146 of the other detector unit 14*a*, the correction function 24*d* corrects an offset of the time information between the detector unit 14*a* as a reference and the other detector unit 14*a*.

According to such a configuration, the image quality of a PET image can be improved by correcting an offset of time information occurring between the detector units 14*a*.

Other Embodiments

Although the embodiment of the PET apparatus 100 has been described above, the embodiment of the nuclear medicine diagnostic apparatus disclosed in this application is not limited thereto. Therefore, other embodiments of the nuclear medicine diagnostic apparatus are described below.

For example, in the embodiment described above, an example in which the correction function 24d uses difference information to correct the detection time included in counting information produced by the FPGA 146 of the detector unit 14a has been described; however, the embodiment is not limited thereto.

For example, the correction function 24d may use difference information and correct time information produced by the TDC 145 of the other detector unit 14a so as to match the time information with time information produced by the TDC 145 of the detector unit 14a as a reference. In this case, for example, the correction function 24d is provided in the FPGA 146 of each detector unit 14a, and the FPGA 146 produces counting information on the basis of the time information corrected by the correction function 24d.

Furthermore, in the embodiment described above, an example in which an offset of time information is corrected between the detector units 14a has been described; however, the embodiment is not limited thereto.

For example, when the PET apparatus 100 includes a plurality of ring-shaped PET detectors arranged in the Z-axis direction, an offset of time information may be corrected between the PET detectors. In this case, the PET detector is an example of the unit of detector.

Moreover, for example, when each detector unit in the PET detector includes a plurality of detector modules arranged in the Z-axis direction, an offset of time information may be corrected between the detector modules. In this case, the detector module is an example of the unit of detector.

Furthermore, in the embodiment described above, the embodiment of the PET apparatus has been described as an example of the nuclear medicine diagnostic apparatus; however, the embodiment is not limited thereto. For example, the technology disclosed in this application can be similarly applied to other nuclear medicine diagnostic apparatuses such as single photon emission computed tomography (SPECT) apparatuses.

Furthermore, in the embodiment described above, an example in which the first production circuitry, the first acquisition circuitry, the second acquisition circuitry, the correction section, and the second production circuitry in this specification are implemented by the processing functions of the processing circuitry has been described; however, the embodiment is not limited thereto. For example, the first production circuitry, the first acquisition circuitry, the second acquisition circuitry, the correction section, and the second production circuitry in this specification may be implemented by the processing functions of the processing circuitry described in the embodiment, or the same processing functions may also be implemented by hardware only, software only, or a mixture of hardware and software.

Furthermore, in the embodiments described above, the processing circuitry is not limited to those implemented by a single processor, but may be configured by combining a plurality of independent processors, and respective processors may implement respective processing functions by executing respective computer programs. Furthermore, the respective processing functions of the processing circuitry may be implemented by being appropriately distributed or integrated into single processing circuitry or a plurality of pieces of processing circuitry. Furthermore, the respective processing functions of the processing circuitry may be implemented by a mixture of hardware such as circuits and software. In the above, an example in which the computer programs corresponding to the respective processing functions are stored in a single memory has been described; however, the embodiment is not limited thereto. For example, the computer programs corresponding to the respective processing functions may be distributed and stored in a plurality of memories, and the processing circuitry may be configured to read the computer programs from the memories and execute the read computer programs.

Furthermore, the term "processor" used in the description of the embodiments described above means, for example, a circuit such as CPU, GPU, ASIC, or a programmable logic device (for example, SPLD, CPLD, and FPGA). Instead of storing the computer programs in the memory, the computer programs may be directly incorporated in the circuitry of the processor. In this case, the processor implements the functions by reading and executing the computer programs incorporated in the circuitry. Furthermore, each processor of the present embodiment is not limited to being configured as single piece of circuitry for each processor, and one processor may be configured by combining a plurality of pieces of independent circuitry to implement the functions thereof.

The computer program executed by the processor is provided by being incorporated in advance in a read only memory (ROM) or the like. The computer program may be provided by being recorded on a computer readable non-transitory storage medium, such as a CD (compact disc)-ROM, a flexible disk (FD), a CD-R (compact disc recordable), and a digital versatile disc (DVD), in a file format installable or executable in these devices. Furthermore, the computer program may be provided or distributed by being stored on a computer connected to a network such as the Internet and downloaded via the network. For example, the computer program is configured as a module including the aforementioned each processing function. As actual hardware, the CPU reads and executes the computer program from the storage medium such as a ROM, so that each module is loaded on a main storage device and produced on the main storage device.

In the embodiments described above, each component of each device illustrated in the drawings is a functional concept, and does not necessarily have to be physically configured as illustrated in the drawings. That is, the specific form of dispersion or integration of each device is not limited to that illustrated in the drawings, but can be configured by functionally or physically dispersing or integrating all or part thereof in arbitrary units, depending on various loads and usage conditions. Moreover, each processing function performed by each device can be implemented in whole or in part by a CPU and a computer program that is analyzed and executed by the CPU, or by hardware using wired logic.

Of the processes described in the embodiments described above, all or part of the processes described as being performed automatically can be performed manually, or all or part of the processes described as being performed manually can be performed automatically by known methods. Processing procedures, control procedures, specific names, and other information including various data and parameters described in the above description and drawings may be changed as desired, unless otherwise noted.

According to at least one of the embodiments described above, an increase in device price and a decrease in reliability due to synchronization between units of detector can be suppressed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine diagnostic apparatus comprising:
a plurality of detector units configured to detect gamma rays, each of the detector units including
detection circuitry configured to detect an analog signal based on a result of detecting the gamma rays,
generation circuitry configured to generate a clock signal, and
first production circuitry configured to produce time information by measuring a time over which an intensity of the analog signal detected by the detection circuitry exceeds a predetermined threshold and converting the time into a digital signal on the basis of the clock signal generated by the generation circuitry, wherein
the plurality of detector units includes a first detector unit and a second detector unit different from the first detector unit, the first detector unit including a first generation circuitry configured to generate a first clock signal, the second detector unit including a second generation circuitry configured to generate a second clock signal, and the generation circuitry comprising the first and second generation circuitry, and
the nuclear medicine diagnostic apparatus further includes:
first acquisition circuitry configured to acquire, on the basis of a synchronization signal generated by synchronization signal generation circuitry, first time information produced by the first production circuitry of the first detector unit, on the basis of the first clock signal;
second acquisition circuitry configured to acquire, on the basis of the synchronization signal, second time information produced by the first production circuitry of the second detector unit on the basis of the second clock signal; and processing circuitry configured to correct an offset of the time information between the first detector unit and the second detector unit on the basis of the first time information and the second time information.

2. The nuclear medicine diagnostic apparatus according to claim 1, wherein
the processing circuitry is further configured to store difference information between the first time information and the second time information in a memory, and correct the offset of the time information between the first detector unit and the second detector unit by using the difference information.

3. The nuclear medicine diagnostic apparatus according to claim 2, wherein
each of the detector units further comprises:
second production circuitry configured to produce counting information including a detection time of the gamma rays on the basis of the analog signal and the time information, and

the processing circuitry is further configured to use the difference information and correct a detection time included in the counting information produced by the second production circuitry of the second detector unit so as to match the detection time with a detection time included in the counting information produced by the second production circuitry of the first detector unit.

4. The nuclear medicine diagnostic apparatus according to claim 2, wherein
the processing circuitry is further configured to use the difference information and correct time information produced by the first production circuitry of the second detector unit so as to match the time information with time information produced by the first production circuitry of the first detector unit.

5. The nuclear medicine diagnostic apparatus according to claim 2, wherein
the first acquisition circuitry and the second acquisition circuitry are further configured to re-acquire the first time information and the second time information after the difference information is stored in the memory, and
the processing circuitry is further configured to verify whether correction of the offset of the time information using the difference information is correctly performed, on the basis of the re-acquired first time information and second time information.

6. The nuclear medicine diagnostic apparatus according to claim 1, wherein
the first acquisition circuitry and the second acquisition circuitry are further configured to, after a rise in power of all the detector units, acquire the first time information and the second time information on the basis of the synchronization signal.

7. The nuclear medicine diagnostic apparatus according to claim 1, wherein
the processing circuitry is further configured to use a linear equation representing a relationship between the time information and an elapsed time defined for each frequency of the clock signal, and correct the offset of the time information caused by a frequency offset of the clock signal between the first detector unit and the second detector unit.

8. The nuclear medicine diagnostic apparatus according to claim 1, wherein
the synchronization signal generation circuitry is a scintillator included in the detection circuitry, the synchronization signal being a gamma ray generated by spontaneous decay of the scintillator, and
the first acquisition circuitry and the second acquisition circuitry are further configured to acquire the first time information and the second time information when the gamma ray due to the spontaneous decay is generated.

9. The nuclear medicine diagnostic apparatus according to claim 1, further comprising:
processing circuitry configured to
reconstruct a PET image on the basis of data on the gamma rays detected by the detector units, and
reconstruct the PET image by using data collected after a detector unit for a last scan to be started starts the scan.

10. The nuclear medicine diagnostic apparatus according to claim 1, wherein
the generation circuitry is an oscillator, and
the first production circuitry is a time to digital converter.

* * * * *